(12) United States Patent
Liu et al.

(10) Patent No.: US 9,733,125 B2
(45) Date of Patent: Aug. 15, 2017

(54) RESONATOR ENHANCED RAMAN SPECTROSCOPY

(71) Applicants: The Penn State Research Foundation, University Park, PA (US); Washington University, St. Louis, MO (US)

(72) Inventors: Zhiwen Liu, State College, PA (US); Lan Yang, Saint Louis, MO (US); Perry Edwards, State College, PA (US); Corey Janisch, University Park, PA (US); Bo Peng, Saint Louis, MO (US); Sahin Ozdemir, University City, MO (US)

(73) Assignees: The Penn State Research Foundation, University Park, PA (US); Washington University, St. Louis, MO (US)

( * ) Notice: Subject to any disclaimer, the term of this patent is extended or adjusted under 35 U.S.C. 154(b) by 94 days.

(21) Appl. No.: 14/431,080

(22) PCT Filed: Sep. 25, 2013

(86) PCT No.: PCT/US2013/061769
§ 371 (c)(1),
(2) Date: Mar. 25, 2015

(87) PCT Pub. No.: WO2014/052502
PCT Pub. Date: Apr. 3, 2014

(65) Prior Publication Data
US 2015/0276481 A1   Oct. 1, 2015

Related U.S. Application Data

(60) Provisional application No. 61/705,405, filed on Sep. 25, 2012.

(51) Int. Cl.
*G01J 3/44* (2006.01)
*G01N 21/65* (2006.01)
(Continued)

(52) U.S. Cl.
CPC ............ *G01J 3/44* (2013.01); *G01J 3/0208* (2013.01); *G01J 3/0224* (2013.01); *G01J 3/10* (2013.01);
(Continued)

(58) Field of Classification Search
CPC ......... G01J 3/44; G01J 3/0208; G01J 3/0224; G01J 3/10; G01J 3/26; G01J 3/2823; G01N 21/65
(Continued)

(56) References Cited

U.S. PATENT DOCUMENTS

| | | | |
|---|---|---|---|
| 8,649,000 B1 * | 2/2014 | Anderson | ............ G01N 21/65 356/51 |
| 2006/0055921 A1 | 3/2006 | Wang et al. | |

(Continued)

OTHER PUBLICATIONS

Ian M. White et al., Demonstration of Composite Microsphere Cavity and Surface Enhanced Raman Spectroscopy for Improved Sensitivity, Chemical and Biological Sensors for Industrial and Environmental Security, 2005, pp. 59940G1-59940G10.
(Continued)

*Primary Examiner* — Hina F Ayub
(74) *Attorney, Agent, or Firm* — Buchanan Ingersoll & Rooney PC

(57) ABSTRACT

Embodiments of the invention provide Raman spectroscopy methods and devices that exploit high quality factor (Q) resonators to enhance Raman signal by several orders of magnitude over the signal typically expected for Raman methods. Embodiments typically include one or more resonators, typically microtoroid microresonators. Embodiments also take advantage of Rayleigh scattering using these microresonators. Embodiments may be particularly useful for non-labeled nanoparticle sensing.

21 Claims, 19 Drawing Sheets

(51) Int. Cl.
*G01J 3/26* (2006.01)
*G01J 3/28* (2006.01)
*G01J 3/02* (2006.01)
*G01J 3/10* (2006.01)

(52) U.S. Cl.
CPC .............. *G01J 3/26* (2013.01); *G01J 3/2823* (2013.01); *G01N 21/65* (2013.01)

(58) Field of Classification Search
USPC ........................................................ 356/301
See application file for complete search history.

(56) References Cited

U.S. PATENT DOCUMENTS

| | | |
|---|---|---|
| 2008/0030726 A1 | 2/2008 | Flanders et al. |
| 2010/0309465 A1* | 12/2010 | Liu ........................... G01J 3/44 356/301 |
| 2011/0122407 A1* | 5/2011 | Jalali ...................... G01N 21/65 356/301 |
| 2011/0139970 A1 | 6/2011 | He et al. |
| 2013/0208272 A1* | 8/2013 | Lettleton ................ G01N 21/65 356/301 |
| 2013/0286380 A1* | 10/2013 | Selker ....................... G01J 3/44 356/51 |

OTHER PUBLICATIONS

PCT/US2013/061769 International Search Report and Written Opinion, The Penn State Research Foundation et al., dated Mar. 6, 2014.

* cited by examiner conventional Raman hyper Raman

FIG. 10(A)
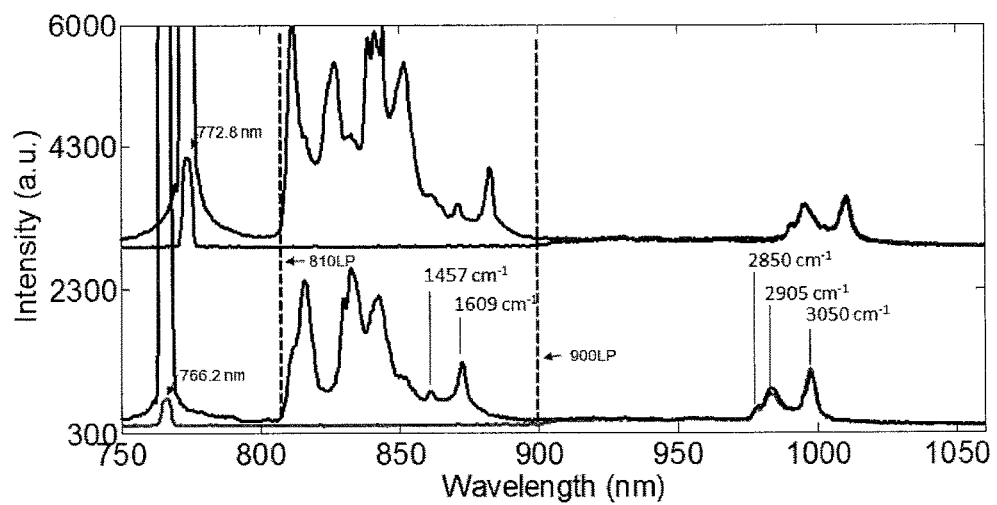
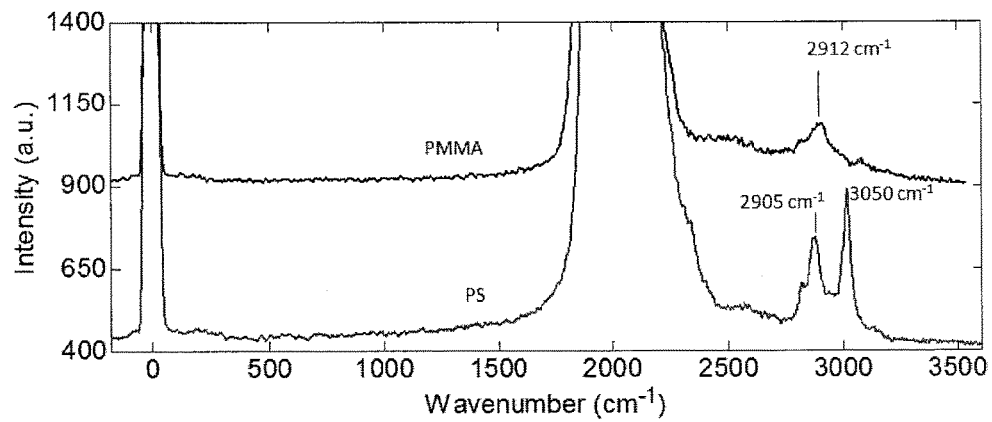
FIG. 10(B)

Fig. 11       FIG. 12
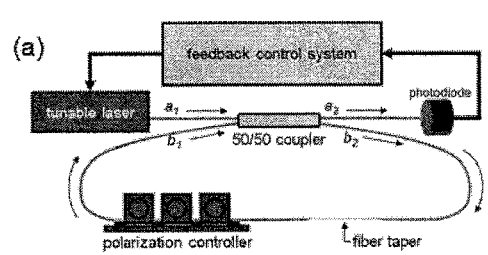
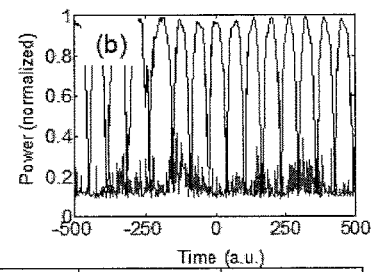
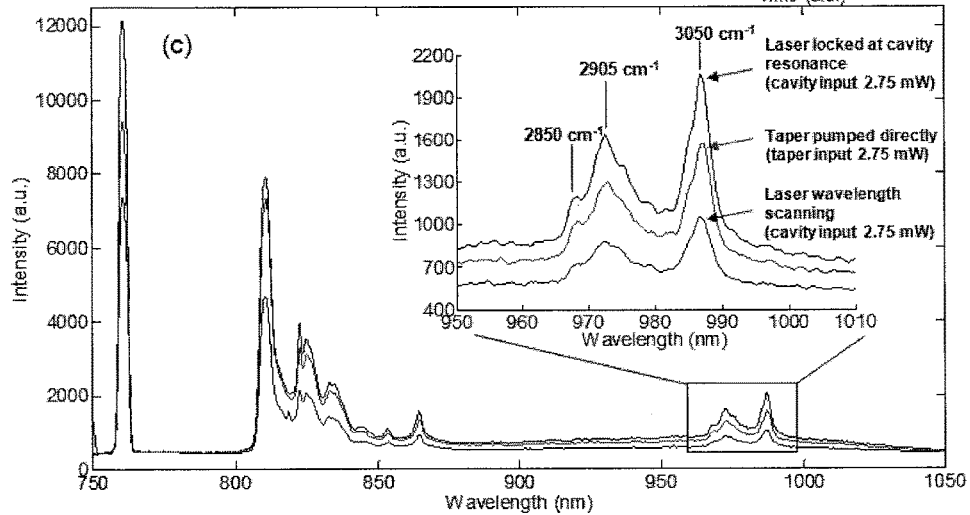
FIG. 13

FIG. 16(A)
FIG. 16(B)
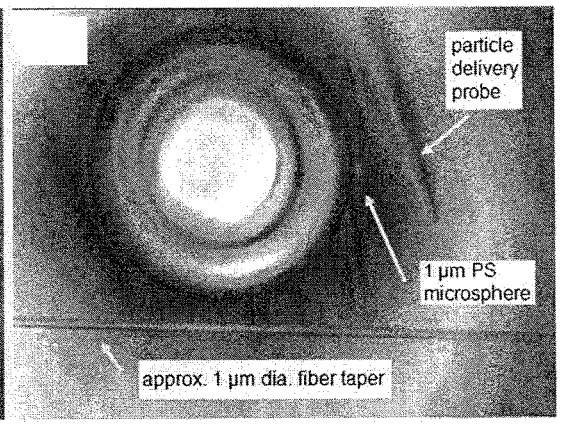

FIG. 18(A)
FIG. 18(B)
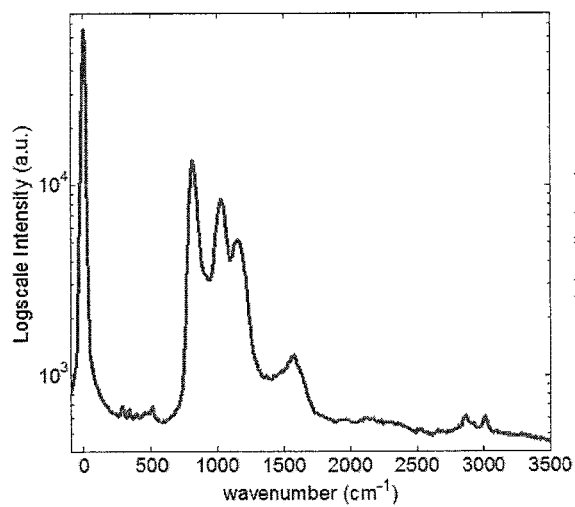
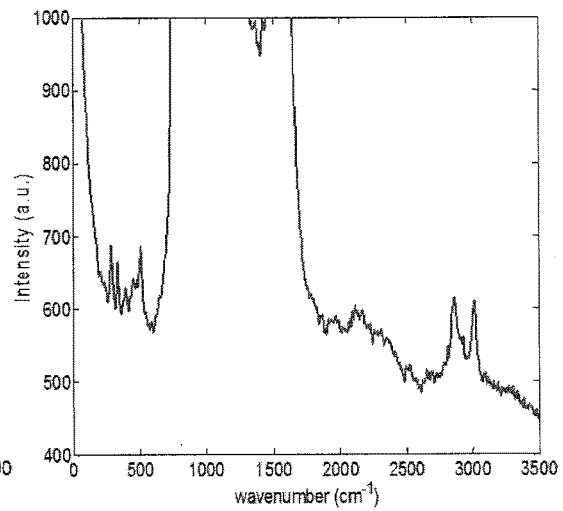

RESONATOR ENHANCED RAMAN SPECTROSCOPY

CROSS-REFERENCE TO RELATED APPLICATIONS

This application is the national phase under 35 U.S.C. §371 of PCT International Application No. PCT/US2013/061769, filed on Sep. 25, 2013, which claims priority to U.S. Provisional Patent App. No. 61/705,405, filed on Sep. 25, 2012, and which is incorporated by reference herein.

STATEMENT REGARDING FEDERALLY SPONSORED RESEARCH OR DEVELOPMENT

This invention was made with government support under Grant Nos. ECCS0547475 and ECCS0954941 awarded by the National Science Foundation, under Grant No. 1U60OH009761-01, awarded by the National Institute of Occupational Safety and Health (NIOSH) and under Contract No. W911NF-12-1-0026, awarded by the U.S. Army/ARO. The Government has certain rights in the invention.

BACKGROUND OF THE INVENTION

Field of the Invention

Embodiments of the invention relate to methods and apparatus for Raman spectroscopy.

Description of the Related Art

Raman scattering spectroscopy is a powerful tool that has found numerous applications in a wide variety of areas ranging from fundamental studies, such as molecular dynamics, to practical applications, such as chemical sensing. The Raman scattering spectrum is molecule specific and can serve as a "fingerprint" to uniquely identify different molecular species. Unfortunately, Raman scattering is usually very weak due to its rather small scattering cross-section (e.g., typical differential scattering cross-section $d\sigma/d\Omega$: $10^{-29}$-$10^{-30}$ $cm^2$/steradian/molecule). Therefore, efforts have been made to enhance the Raman scattering signal.

Although significant advances have been made to Raman signal enhancement, further work remains.

BRIEF DESCRIPTION OF THE INVENTION

With the increasing presence of nanoparticles in daily lives, there is a growing interest in assessing their benefits and risks. Meanwhile, there is also a strong need to detect and characterize biological nanoparticles such as molecules, proteins and viruses which have significant impact on human health and environmental monitoring. A critical step in this assessment is to develop a label-free, reliable and ultra-sensitive technique for real-time and onsite detection, characterization, identification and measurement of individual viruses and nanoparticles. This will facilitate studies of physical and biological properties of single viruses, size and material dependent properties of nanoparticles at single particle level.

One of the most widely used non-invasive methods to measure nanoparticle smaller than 100 nm is based on elastic light scattering technique, also known as Rayleigh scattering. For ensemble measurement of large quantities of nanoparticles of the same kind, it could measure particles smaller than 1 nanometer; however, at single particle level it is limited to particles of 50 nm or above in diameter. On the other hand, Raman spectroscopy based on inelastic scattering process is a general technique to obtain 'molecular fingerprint' to identify the chemical composition in a material system. Analyzing nanoscale objects, such as nanoparticles, biomolecules and proteins, in trace amount is challenging as a result of the low scattering intensity due to the small sample size. The present disclosure merges the two different techniques, i.e., Rayleigh scattering spectroscopy for particle counter and Raman spectroscopy in a single platform in a compact or portable design. Achieving in-situ detection, counting, molecule-specific recognition, and size measurement simultaneously using a single platform will have significant impact to many fields including but not limited to environmental monitoring, disease diagnosis, and biosensing.

We provide a new class of nanoparticle sensing system based on Rayleigh and Raman scattering effect in ultra-high quality factor (Q) optical micro-resonators. This achieves not only ultra-sensitive detection but also identification and measurement of particles and molecules in air or dispersed in a liquid environment at single particle resolution. On one hand, Rayleigh scattering in resonators leads to change of resonator properties (e.g., resonant frequencies and linewidths, mode profiles), resulting in phenomena such as self-reference mode-splitting that can be utilized to detect and accurately measure nanoparticles down to several nm in size. On the other hand, Raman scattering, which is greatly enhanced by several orders of magnitude in a ultra-high-Q microresonator, provides identification of molecules/particles through recognition of their spectral fingerprints of molecular vibrations.

Our technique uniquely allows integration of Raman spectroscopy (i.e., ultra-high-microresonator-enhanced spontaneous Raman, Raman optical activity, hyper Raman, coherent anti-Stokes Raman, and stimulated Raman, where the signal can be enhanced by several orders of magnitude over the signal typically expected for conventional Raman methods; in some embodiments Q can be as high as $10^8$-$10^9$) with Rayleigh scattering induced phenomenon in an ultra-high-Q Whispering Gallery mode (WGM) microresonator. The former effect provides identification of molecules/particles through molecular vibrational spectroscopy, while the latter phenomenon helps detect and accurately measure the nanoparticles/molecules utilizing interactions of nanoparticles with the WGMs. By integrating Raman and Rayleigh effects together, we achieve a multi-function sensing unit capable of ultra-sensitive real-time, in-sit detection, identification and measurement of single nanoparticles (such as polymers, micelles, carbohydrates, nanoparticles, colloidal dispersions and molecules, etc) in a single-shot measurement.

Compared with the pump power outside of a resonator, the optical power circulating inside the resonator is significantly enhanced by a buildup factor. For example, in a microtoroid or microsphere whispering gallery mode microresonator the buildup factor G is given by:

$$G = \frac{\lambda Q_{ex}}{\pi^2 R n \left(1 + \frac{Q_{ex}}{Q_0}\right)^2} \quad (1)$$

where $\lambda$ is the vacuum wavelength, n denotes the effective refractive index, R is the radius of the resonator, which could be in various forms, including but not limited to microtoroid, microring, microdisk, or microsphere; $Q_0$ is the intrinsic quality factor, and $Q_{ex}$ is the quality factor accounting for the external coupling loss. As an example, $G \sim 10^5$ can be achieved for $Q_{ex} \sim Q_0 \sim 2 \times 10^8$, R~20 µm, n~1.45, and λ~0.8 µm. Since the spontaneous Raman signal linearly depends on the excitation power, Raman scattering signal from a nanoparticle adsorbed onto the microresonator can hence be potentially enhanced by five orders of magnitude. Similarly, significant enhancement can also be realized in other type of Raman measurements including but are not limited to hyper Raman and coherent Raman (e.g., coherent anti-Stokes Raman scattering, stimulated Raman scattering) processes.

In preferred embodiments the high quality factor resonators are microtoroid resonators, but those skilled in the art will recognize that additional resonators may be used. For example, although the following discussion is mainly focused on microtoroid resonators it should be noted that the same concept and technique can also be applied using other types of resonators. These include, for example, but are not limited to microspheres, microbubbles, micropost, microdisk, metamaterials and photonic crystal cavity, Fabry Perot type resonator, and ring resonator.

It should also be emphasized that the molecules and particles that may be detected by systems of the invention need not be labeled. Further, in some embodiments the microresonator may be tunable to allow the pump and Raman signal to be resonant.

DETAILED DESCRIPTION OF THE FIGURES

FIG. 1 shows a schematic diagram of a proposed ultrahigh-Q microresonator enhanced Raman spectroscopy experimental system (device/instrument sizes are not in scale).

FIG. 2(A) and FIG. 2(B) show preliminary results of Raman spectra of microsphere adsorbed on microtoroid microresonantor. FIG. 2(A): Measured spectra for a 2-µm polystyrene microsphere on a microtoroid when the pump laser was tuned to near 759 and 766 nm, The inset shows relative frequency shift of the Raman signal, which is independent on the pump wavelength. A signature Raman peak for polystyrene at 3060 cm$^{-1}$ can be observed. FIG. 2(B): Raman spectrum with a 30-second integration period at a pump wavelength of 763.5 nm.

Figure 6A:
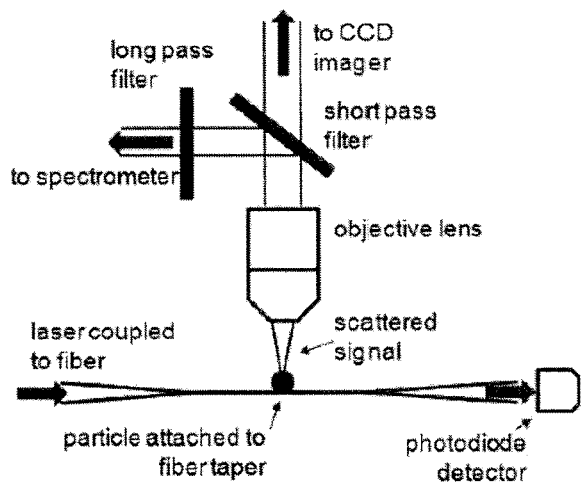
Figure 6B:
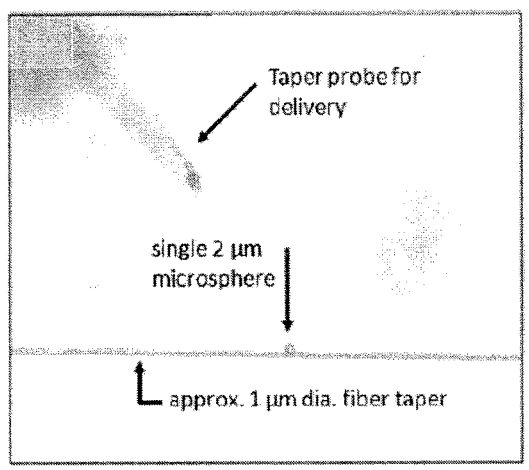
Figure 6C:
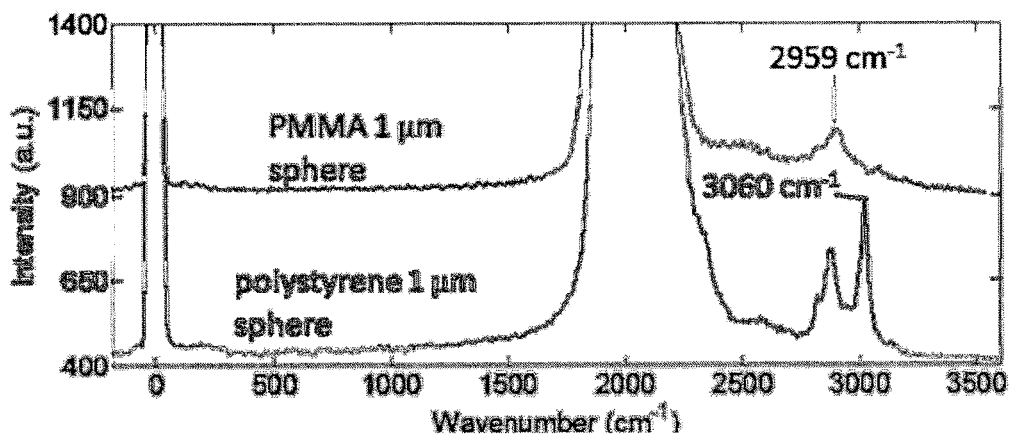
Figure 6D:
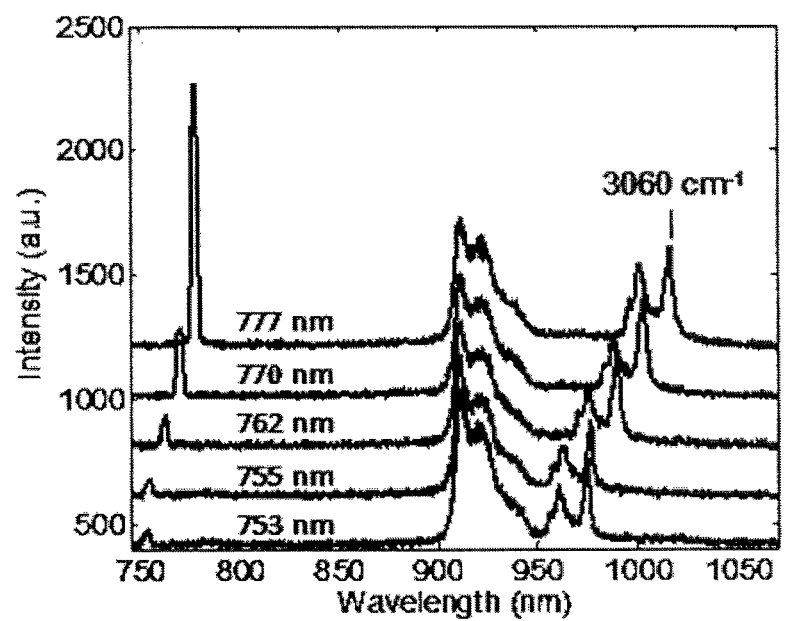

FIG. 6(A) shows a schematic diagram of an experimental setup; FIG. 6(B) shows an image of a 2 µm polymer microsphere delivered and adhered to a 1 µm taper; FIG. 6(C) shows a Raman spectra obtained for, in a 1 µm PS microsphere while tuning the pump wavelength (inset shows Raman shift), and FIG. 6(D) shows a Raman spectra of 1 µm PS and PMMA microspheres attached to a fiber taper.

Figure 7:
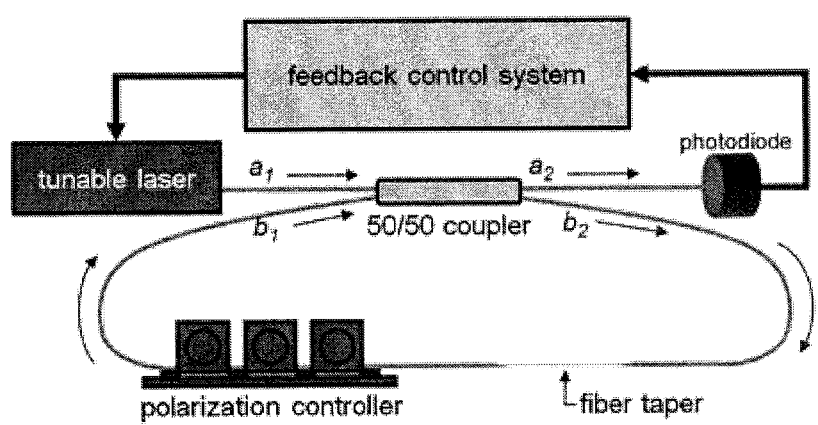

FIG. 7 shows a schematic diagram showing an embodiment of fiber ring resonator enhanced Raman spectroscopy. The fiber ring resonator is composed of a fiber coupler, a fiber taper, and a polarization controller.

Figure 8:
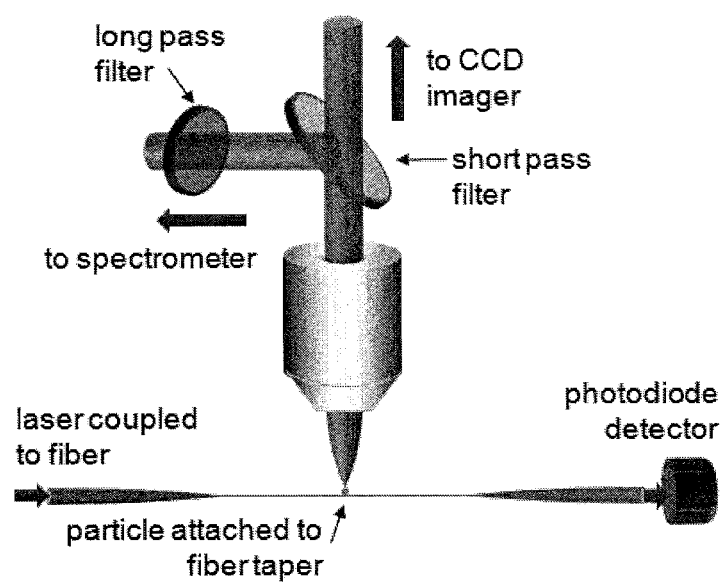

FIG. 8 shows a schematic diagram of the experimental setup where scattered signal from a particle attached to a fiber taper is collected by a long working distance objective and analyzed by a spectrometer.

Figure 9:
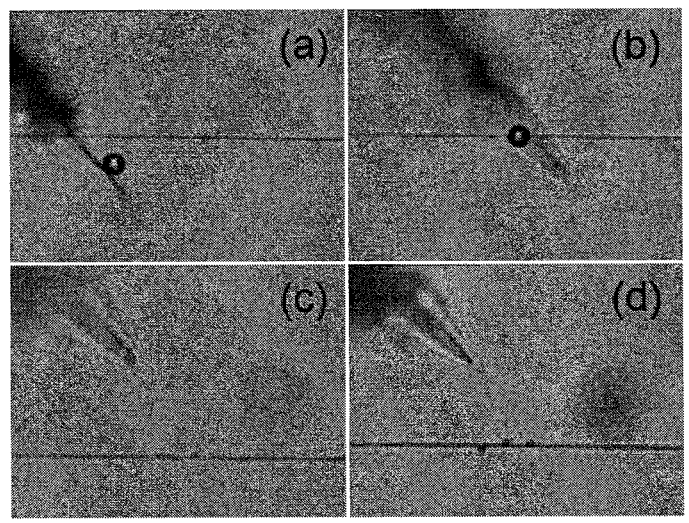

FIG. 9 shows a series of images demonstrating single and multiple particle delivery in four parts. In part (a), a 10-µm microsphere is attached to a fiber probe and moved nearby a fiber taper; in part (b) the 10-µm microsphere is attached to the fiber taper and held in place by electrostatic force; in part (c) a 2-µm PS sphere is attached to a fiber taper; in part (d) several microspheres are delivered to a fiber taper.

FIG. 10(A) shows Raman spectra obtained for a 2 µm PS microsphere while tuning the pump wavelength from 766.2 nm (bottom) to 773.8 nm (top) with a 900 nm long pass filter in the system. The overlapping top curves for each wavelength position were captured by switching to a shorter long pass filter (810 nm) to demonstrate the existence of the silica Raman background. The PS Raman peaks are labeled with their observed Raman shifts.

FIG. 10(B), shows spectra obtained for 1 µm PS (bottom) and 1 µm PMMA (top) microspheres attached to a fiber taper and aligned according to Raman shift.

FIG. 11 shows a schematic of fiber ring resonator and wavelength locking setup. The fiber ring resonator is composed of a 50/50 fiber coupler, the fiber taper, and a polarization controller.

FIG. 12 shows a comparison of locking (bottom) and unlocked transmission time-series plots (top). The unlocked time-series was acquired while wavelength scanning.

FIG. 13 shows a comparison of Raman spectra for a 2 µm PS sphere attached to a fiber taper for the cases of wavelength locking (top), laserwavelength constantly scanning in the cavity configuration (top) and taper only excitation (bottom). Each spectra was recorded using 2.75 mW input power and 30 second integration times.

Figure 14:
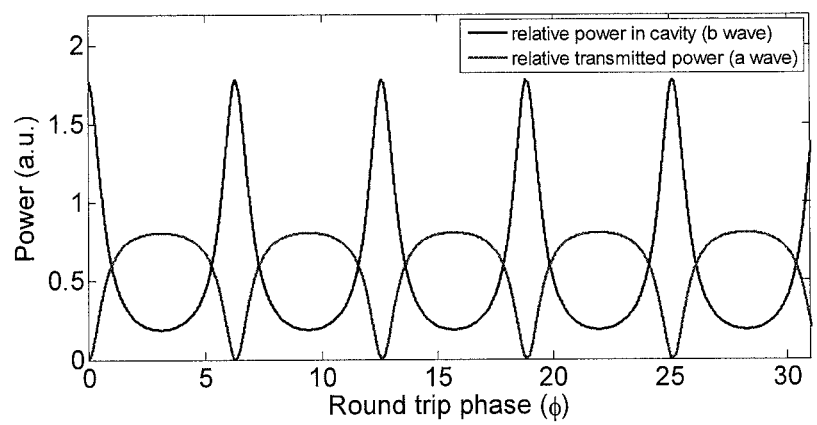

FIG. 14 shows a simulation of fiber ring cavity using coupling conditions similar to experimental ring cavity.

Figure 15:
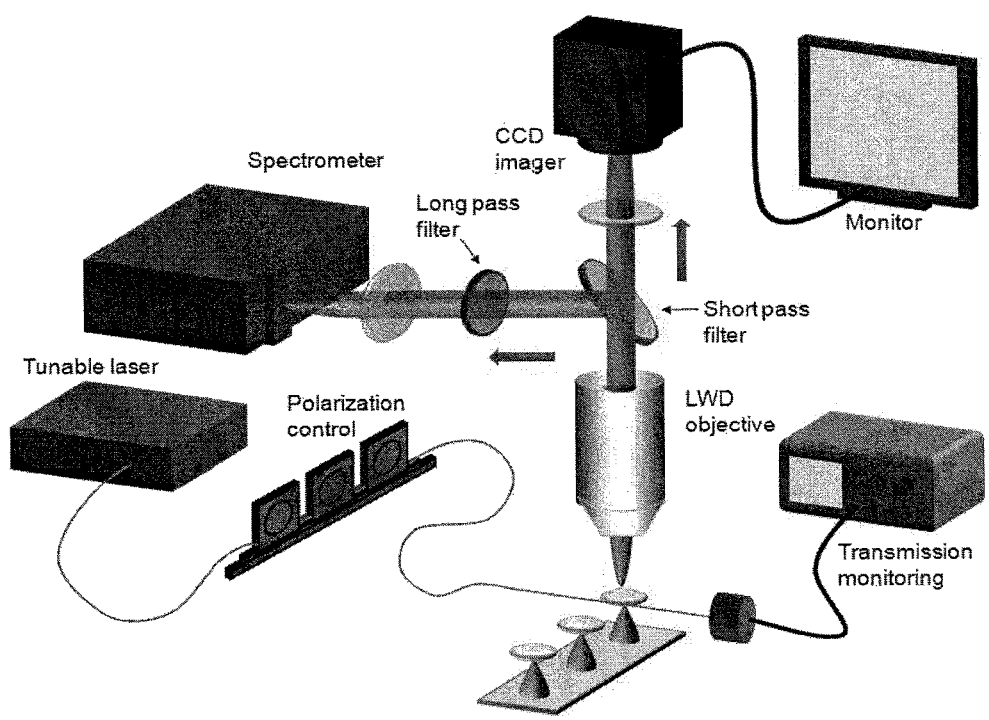

FIG. 15 is a schematic diagram of the experimental setup for collecting scattered signal from particles adhered to microtoroids. The fiber taper is coupled to a tunable diode laser and transmission is monitored for monitoring toroid modes and for wavelength locking.

FIG. 16(A) shows bright field image of microtoroid and taper aligned for coupling (out of focus). FIG. 16(B) shows particle attachment to a microtoroid. A single 1-µm polystyrene microsphere is adhered to the side wall of the microtoroid via delivery from a tapered probe.

Figure 17A:
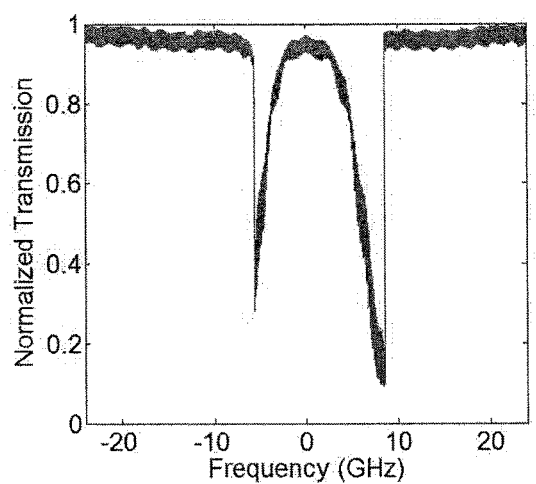
Figure 17B:
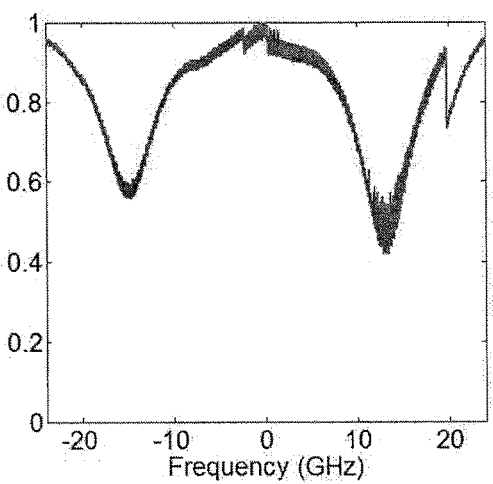

FIG. 17(A) shows a microtoroid mode for down-scan (negative frequencies) and up-scan (positive frequencies) of the pump wavelength. FIG. 17(B) shows the same modes as FIG. 17(A) after a 1-µm polystyrene microsphere is placed on the microtoroid.

FIGS. 18(A) and 18(B) show Raman spectra obtained from a 30 second integration (5 mW coupled pump laser) of signal from a 1-µm polystyrene sphere placed on a microtoroid. The plot in FIG. 18(B) shows a zoomed in portion of FIG. 18(A), where the characteristic Raman peaks for polystyrene are easily observed. Pump laser locked at 761.6 nm.

Figure 19A:
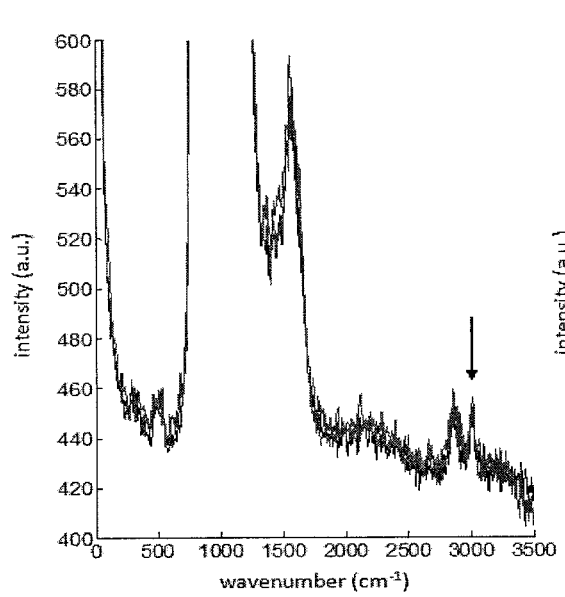
Figure 19B:
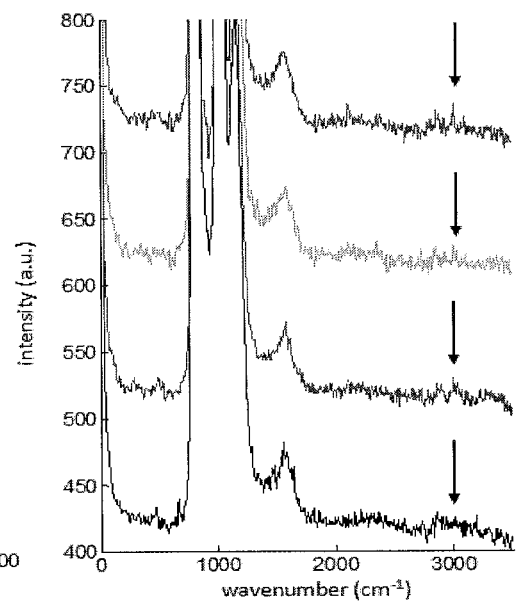

FIG. 19(A) shows Raman spectra obtained from a 5 second integration (5 mW coupled pump laser) of signal from a 1-µm polystyrene sphere placed on a microtoroid. Three separate data sets are overlaid to demonstrate repeatability of signal collection. FIG. 19(B) shows a zoomed in portion of FIG. 19(A), where the characteristic Raman peaks for polystyrene are observed near 3060 cm$^{-1}$. Raman spectra obtained from a 2 second integration using the same conditions as in FIG. 19(A). The arrow indicates on each spectrum where the same characteristic 3060 cm$^{-1}$ Raman peak of polystyrene is located. The Raman peak is difficult to discern from the background at this short of integration time. The pump laser was locked at 761.6 nm for these measurements.

DETAILED DESCRIPTION OF THE INVENTION

Techniques and equipment of the invention may be used with any of a variety of Raman spectroscopy methods and equipment. A number of exemplary embodiments are described below.

I. General Raman Spectroscopy Using Whispering Gallery Microresonators

Embodiments provide Raman spectroscopic sensing using whispering gallery microresonators as a label-free method for single particle detection. Whispering gallery mode microresonators are used as platforms to perform sensitive particle detection by exploiting the strong, evanescent field of a resonant mode exposed on the surface of the microresonator. Particles adhered to the microresonator surface interact with the field and scatter photons circulating within the resonator. In particular, Raman scattered photons are detected, providing molecular-specific "fingerprint" information regarding the adhered particles. The exploitation of a resonant mode allows for enhancement of generated Raman signal over traditional methods of spontaneous Raman scattering.

Optical microresonators, in particular whispering gallery mode (WGM) microresonators, have emerged over the last decade as extremely sensitive, compact sensors that have been explored for their applications towards healthcare, pharmaceuticals, environmental monitoring, defense and security. Additionally, microresonators have been demonstrated as useful devices in other applications such as high resolution spectroscopy, optical filters, frequency stabilizers, and optical switching. Microresonator based sensing has several key advantages, which are primarily due to their high quality factor ($Q>10^8$) and small mode volume. First, microresonators are capable of trapping a significant amount of light using low-power resonant pump lasers for an extended period of time (nanoseconds). Second, microresonators can confine the light energy in extremely small mode volumes creating the high intensity circulating field. Third, the circulating light within the resonator has an evanescent field that extends outside the resonator, and thus can interact with the surrounding medium or molecules on the resonator surface. The intense resonating mode can therefore be exploited for strong light-sample interaction, which can be utilized for sensing through a variety of techniques. In this disclosure, whispering gallery mode microresonators are demonstrated as useful platforms for performing label-free Raman based particle sensing.

Raman spectroscopy can provide molecule-specific detection of particles adhered to the surface of microresonators. While several methods for WGM microresonator sensing also provide molecular specificity, Raman spectroscopy offers the capability to uniquely identify adhered particles via analysis of the chemical "spectral fingerprint," and without the aid of fluorophores used for example in fluorescence detection. On the other hand, Raman scattering is usually very weak due to its rather small differential scattering cross-section. The small scattering cross-section is a limitation in sensing, as many Raman spectroscopy applications require a relatively high power pump laser to generate sufficient signal, and sensitive detector systems for signal collection and analysis. Coherent Raman spectroscopy techniques offer orders of magnitude improved sensitivity but require multiple excitation beams and more complex system geometries. WGM microresonators can provide extremely intense light fields at their surface using low laser pump powers enabling the capability for significant signal enhancement. The strong circulating power within a microresonator effectively alleviates the need for a high power pump laser system.

Other Raman enhancement techniques, such as surface enhanced Raman scattering (SERS), have demonstrated significant enhancement of spontaneous Raman signal for sensing applications. WGM resonator sensing has been described and demonstrated using SERS to locally enhance sample interaction with the resonating pump field.

Embodiments may utilize pure resonant mode to enhance Raman signals. A significant advantage of this method is that the optical modes in microresonators, in particular microtoroids, are highly controllable and reproducible. Microtoroids fabricated on the same chip tend to have similar resonant frequencies and quality factors. In addition, each microresonator can be accurately characterized in situ before utilizing as a Raman sensor. The ability to fully control and characterize the optical mode makes microresonator enhanced Raman ideal for quantitative analysis of adhered particles, such as for measuring the concentrations of target molecular species. Furthermore, integration of enhanced Raman sensing with microresonators and other resonator sensing methods (e.g., quantitative detection through absorption, mode-splitting would allow for comprehensive physical and chemical characterization to detect, identify and measure particles.

Cavity buildup can be significant to this development. Particles adhered to the surface of a high-Q microresonator interacting with the resonant circulating mode can experience orders of magnitude effective higher intensity compared to the intensity of the coupled pump laser. This is due to the longtime presence of circulating photons, which can buildup within the microresonator. The effective resonating power within the cavity Pc is related to the input power Pin (Pc=BPin), where B represents the buildup factor within the cavity. The buildup factor for microresonators can be derived using the expressions for the intrinsic and extrinsic Q's ($Q_{ex}$ and $Q_0$ respectively) of a microresonator. The buildup factor can be written as, $$\frac{Q_{ex}}{\left(\frac{Q_{ex}}{Q_O}+1\right)^2}\frac{4\Delta v}{\omega}$$

Where $\Delta v$ is the cavity free spectral range (or FSR). If critical coupling is achieved ($Q_O \approx Q_{ex}$) at resonance (w=w0), the buildup factor can then be expressed as, $$B=\frac{\lambda Q_O}{\pi^2 nR}$$

where n is the refractive index, R is the radius of the microresonator, and $\lambda$ is the vacuum wavelength. Eq. 2 indicates that a resonator with a Q-factor of $\sim 10^8$, achievable with a microtoroid resonator, and a diameter of 40 μm (also n=1.45, $\lambda \sim 780$ nm), when driven at resonance with critical coupling, can achieve a buildup factor of $B=10^5$. Since Raman scattering signal scales linearly with excitation power, it potentially can be enhanced by the same buildup factor.

One embodiment and experimental system is depicted in the diagram in FIG. 15 and images shown in FIG. 16(A) AND FIG. 16(B). The microtoroids are evanescently coupled to a fiber taper, which is pumped by a tunable diode laser (<130 kHz linewidth). The polarization state of the laser can be optimized for coupling into a microtoroid by an in-line fiber based polarization controller, as the frequency of the laser is tuned to excite a high-Q mode in a microresonator. The transmission of the fiber taper is also monitored, and can be used as a feedback signal to lock the laser to the resonant frequency of the microtoroid.

When a microresonator is positioned near the fiber taper for coupling to a resonator mode (as shown in FIG. 16(A)), the pump laser is first continuously scanned. Once a desired resonant mode of a microresonator has been located by coarse tuning of the operating wavelength of the laser, the mode is characterized by continuous fine-tune scanning of the laser wavelength and monitoring the transmission of the laser on an oscilloscope. This method allows optimization of the physical coupling (taper-toroid gap, polarization) of the resonant mode. Once the desired coupling is achieved, the laser system control is switched to computer controlled wavelength locking hardware operated by a LABVIEW algorithm. By locking the laser wavelength to the cavity resonance, particles adhered to the microresonator surface can continuously interact with the circulating cavity field. Similar methods for wavelength locking are demonstrated elsewhere. The LABVIEW program tracks the resonance mode of the microresonator by adjusting the laser operating wavelength.

To deposit micro-particles onto the resonator, a fiber taper probe is brought in contact with several microspheres to coerce electrostatic adhesion to the probe. The probe is then used to deposit single particles onto the surface of the microtoroid resonator by bringing the probe in contact with the resonator. FIG. 16(B) shows an image demonstrating placement of a 1-µm onto a microtoroid. The taper probe placement works well for depositing particles down to 1-µm, while other methods exist for simulating the conditions for nano-particle placement and detection (e.g. DMA sorting particle depositors). Additionally, the method used allows controlled manipulation of particle position on the surface of the microresonator. The particle can be placed and removed several times in the same location by using a taper probe.

An imaging and signal collection system was constructed (as depicted in FIG. 15) to simultaneously monitor the taper-microtoroid coupling position while collecting scattered signals from particles adhered to the microtoroid surface.

A long-working distance objective lens is used for both signal collection and imaging in the vertical direction. Collected signals scattered from particles adhered to microtoroids are collected by the objective lens and directed through a long pass filter (to filter the residual pump laser) to a spectrometer for analysis.

Embodiments may be better understood with reference to an example. Here, a microtoroid, approximately 80 µm in diameter, was evanescently coupled to a tapered optical fiber, which guided the laser pump field to the microtoroid. The sensitivity of the experimental system is investigated using a 1-µm polystyrene microsphere placed on a microtoroid. The 1-µm size sphere is selected to provide scattering signal and determine the existence of Raman peaks associated with known spectra of a polystyrene microsphere (peak at 3060 $cm^{-1}$).

A microtoroid resonant mode with $Q\sim10^6$-$10^7$ was selected for use, while the taper-toroid gap was maintained slightly undercoupling (i.e., coupling loss was slightly smaller than the intrinsic loss of the resonator) as the taper tended to be easily drawn towards the surface of the toroid during these measurements. In FIG. 17(A), the mode is shown before placement of the microsphere. The negative scan frequencies indicate down-scan of the pump laser wavelength, while the positive scan frequencies indicate up-scan of the pump laser wavelength. The difference in shape (up scan versus down scan) and the sharp dip with small-scale oscillations on mode can be attributed to thermal-optic effect due to the high power coupled to the high-Q mode of the resonator (~5 mW pump power). In FIG. 17(B), the same mode is shown after placement of the 1-µm microsphere. Here, a significant drop in the Q is observed ($Q\sim5\times10^4$) due to a reduction in the intrinsic Q from additional scattering losses from the microsphere.

With the 1-µm microsphere deposited on the surface of the microtoroid, wavelength locking was engaged for the resonant mode (at approximately 761.6 nm) shown in FIG. 17(B). FIG. 18(A) and FIG. 18(B) show spectra obtained from a 30 second integration of the collected signal. In FIG. 18(A), the features of a strong silica Raman background can be observed at less than 2000 $cm^{-1}$ while much weaker signature Raman peaks of polystyrene are observed near 3060 $cm^{-1}$. The strong silica background can be attributed to scattering of the silica Raman generated in the microtoroid, which is peaked at around 440 $cm^{-1}$ (i.e., 13.2 THz). FIG. 18(B) shows a zoomed in portion of the spectra in FIG. 18(A), where the Raman peaks are more easily observed.

To further investigate the sensitivity for detection, much shorter signal acquisition times were used for recording spectra reported in FIG. 19(A) and FIG. 19(B). In FIG. 19(A), similar spectral signatures for polystyrene are distinguishable from the background with only 5 seconds integration. Several spectra are overlaid in the figure to demonstrate the repeatability of the measurement. FIG. 19(B) shows four spectra acquired using 2 second integration periods. Raman peaks for polystyrene are observed barely above the background noise, however are difficult to discern from the background for repeated measurements. This fluctuation can be attributed to variations in wavelength locking and taper-toroid coupling.

As shown above, we provide an initial investigation of Raman signal generation from microparticles adhered to a microtoroid resonator. This shows the ability to excite Raman scattering from microspheres adhered to the surface of a microtoroid. This indicates the particles interact with the circulating resonate mode of the microtoroid. Signature Raman peaks from signal generated from 1-µm polystyrene microspheres with repeatable measurements made with acquisition times as low as 5 seconds. This is particularly exceptional when one considers that the resonant modes utilized above do not fully take advantage of the capability of high-Q microtoroids. The Q of the modes used in the measurements were approximately $10^4$-$10^5$, which is far less than that of a high-Q toroid mode (~$10^8$) utilized in other embodiments.

The lower Q modes have broader line widths, and the selection of these modes was done in part to more readily achieve wavelength locking. However, this significantly reduced the anticipated build-up factor for the taper-toroid coupling system and reduced the sensitivity of the system. Additionally, the coupling to the resonant modes was not optimal, in the above example, reducing the amount of energy transferred to the resonator. Near 100% coupling efficiency can be achieved for critical coupling through additional optimization of the setup. Also, the detection hardware can be greatly improved. The spectral sensitivity of the CCD detector for the spectrometer is reduced significantly at the wavelengths used for detecting the Raman signal.

II. Resonator Enhanced Spontaneous Raman Spectroscopy

A. General Resonator Enhanced Spontaneous Raman Spectroscopy

Compared with other Raman enhancement techniques (e.g., surface enhanced Raman scattering), a significant advantage of microresonator enhanced Raman is that the optical mode is highly controllable and reproducible. This can be achieved through precision fabrication of the microresonators using standard lithography techniques or other nanofabrication process.

In some embodiments one or more microresonators are to be fabricated on a chip or chips. Both the resonant frequencies and quality factors of individual resonators can be accurately characterized in situ before the Raman measurement. This may be determined, for example, by coupling a tunable laser to an optical fiber which has been tapered to a diameter on the order of the laser wavelength, then positioning the tapered region of the fiber near the resonator exposing the resonator to the evanescent tail of the guided light. Through efficient evanescent mode coupling (optimizing the taper-resonator distance and tuning the laser frequency) and monitoring the fiber transmission, resonator modes of the microcavity can be determined and the quality factor for each mode can be obtained based on the resonant mode linewidth, among other methods.

The polarization state of the optical mode can also be controlled by taking advantage of the fact that the transverse magnetic (TM) and transverse electric (TE) modes have different resonant frequencies and can be selectively excited by tuning the frequency of the laser and controlling its polarization state through the use of an in-fiber polarization controller. This allows for the study of the polarization properties of the Raman signal, which may be used, for example, for chiral analysis. With the ability to fully control and characterize the optical mode, the proposed resonator enhanced Raman is ideal for quantitative analysis, such as measuring the concentrations of target molecular species, opening a new paradigm for label-free ultrasensitive chemical sensing.

Figure 1:
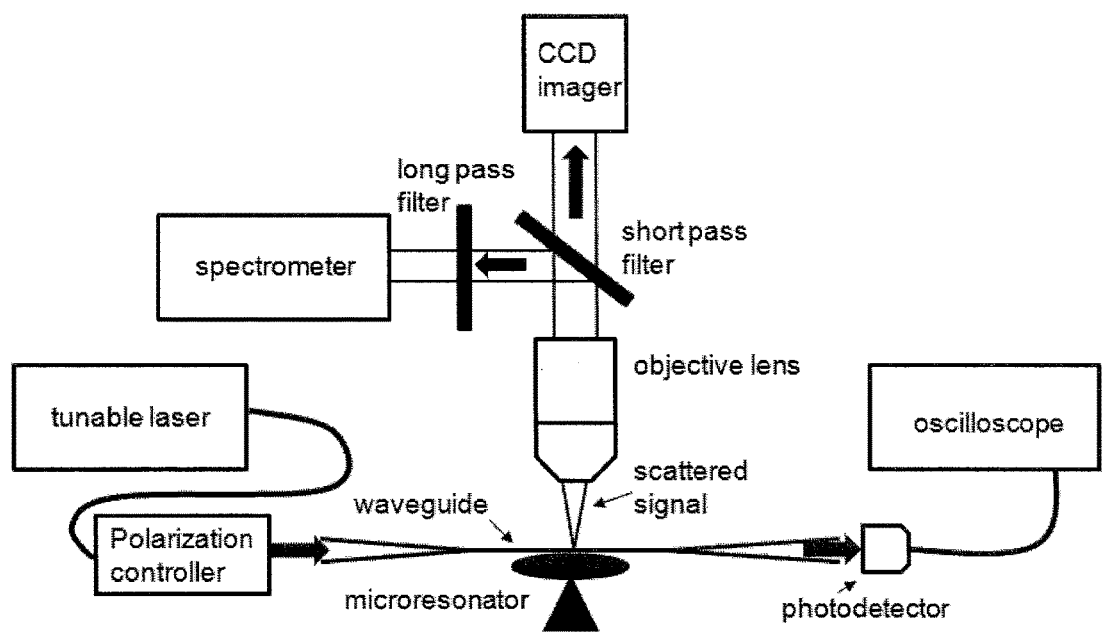

Although it should not be construed as limiting of the claims, an embodiment of the invention may be further understood by recourse to the figures. FIG. 1 shows a schematic diagram of one proposed Raman experimental system. A pump beam is coupled into a microtoroid microresonator through a fiber taper. The polarization state is optimized by an in-fiber polarization controller and the frequency of the laser is tuned to excite a TE or TM mode in the microresonator. The transmission of the fiber taper is also monitored, and can be used as a feedback signal to lock the laser to the resonant frequency of the microresonator. An adsorbed nanoparticle(s) can scatter photons inelastically. The scattered Raman signal is collected by using an objective lens, filtered, and detected by a spectrometer. The scattered Raman signal may also be collected using a similar lens, filter, and spectrometer at different scattering angles. Additionally, in some cases the generated Raman signal may be collected directly through the same coupling fiber taper, leading to a more compact and all-fiber based system.

Figure 2A:
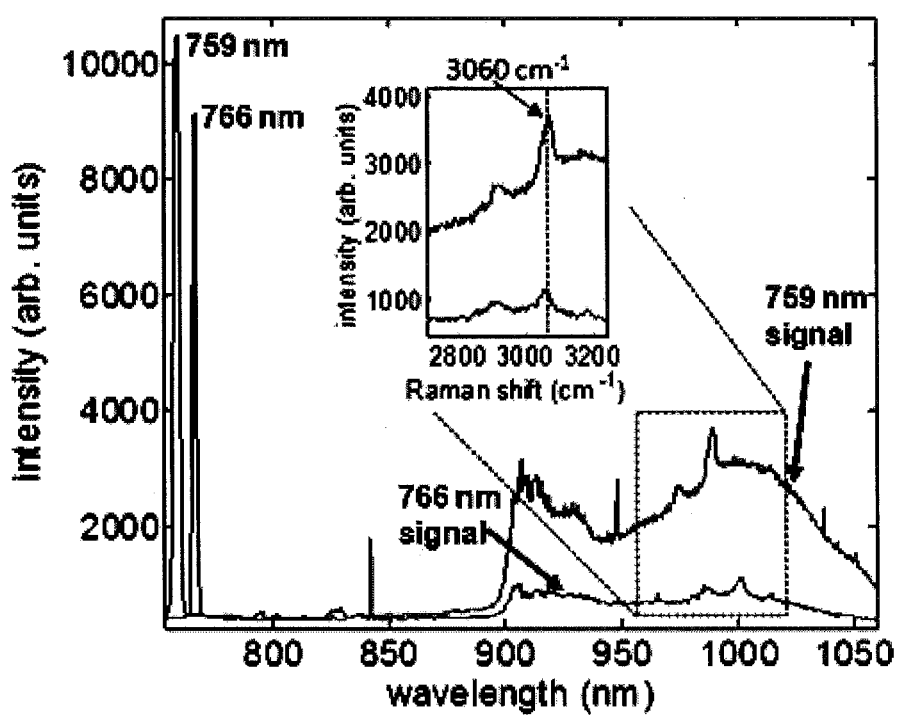

We have developed an experimental system (shown in FIG. 1) to conduct preliminary study of Raman scattering from a microsphere adsorbed on a microtoroid microresonator. FIG. 2(A) shows measured spectra for a 2-μm polystyrene microsphere on a microtoroid (approximately 80 μm diameter) when the pump laser was tuned to near 759 nm and 766 nm, respectively. As can be clearly seen, when the pump wavelength is shifted the wavelength of the Raman signal is shifted accordingly. The relative frequency shift, on the other hand, is independent of the pump wavelength as shown in the inset.

Figure 2B:
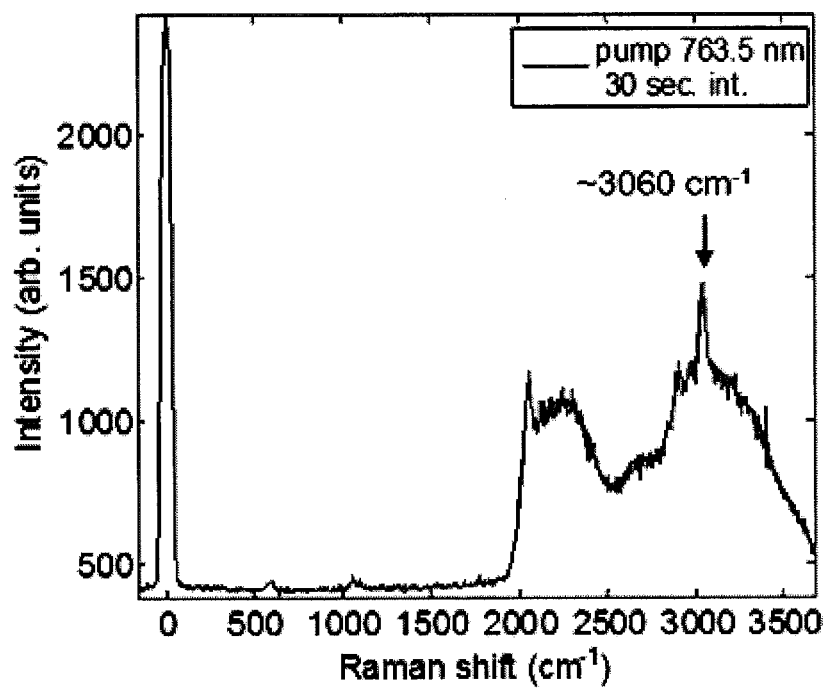

A signature Raman peak for polystyrene at 3060 cm$^{-1}$ can be observed, which agrees with our previous reported Raman and coherent anti-Stokes Raman scattering (CARS) measurements. During the measurements, the laser was set to scan across the resonant mode at 60 Hz (by using a piezo actuator) with approximately 12% of the scan on resonance. For each of these cases, pump power propagating through the fiber taper was set to approximately 7.5 mW. For the spectra acquired at 759 nm pump, an integration time of 300 seconds was used and the 766 nm pump spectra was acquired using 180 second integration. The system was further optimized and FIG. 2(Bb) shows a more efficient Raman signal acquisition with a 30-second integration period at a pump wavelength of 763.5 nm.

Further modifications may be made to some embodiments of the invention. For example, in some embodiments laser frequency is continuously scanned, while in preferred embodiments it is locked to a resonant frequency of the microresonator. With continuous scanning, the microtoroid or other resonator is off-resonant most of the time and only a small fraction of the integration time actually contributes to the measurement. This is useful for characterizing the resonator but not as useful for resonator-enhanced Raman measurements. With a locked frequency significantly more integration time contributes to the measurement.

Both low-Q and high-Q modes may be effective. Low-Q modes have broader linewidths and are therefore easier to achieve frequency-matching with the laser; they may have Q factors in the range of $10^3$-$10^5$. This is significantly less than the high Q values (between $10^8$ and $10^{11}$) that can be achieved in microtoroid resonators or other resonators.

During measurements in some embodiments the fiber taper (used to deliver the pump) is physically in contact with the resonator (i.e., operating in the over-coupling regime). This helps to suppress and isolate the effect of any environmental perturbation to the coupling, particularly when measurements require a long integration time. Note that near 100% coupling efficiency can be accomplished at the critical coupling condition at which the coupling balances the resonator loss. Critical coupling can be accomplished by optimizing the gap distance between the coupling fiber taper and the microresonator.

In our preliminary study, we also observed a background due to scattering of the silica Raman generated in the microtoroid, which is peaked at around 440 cm$^{-1}$ (i.e., 13.2 THz). A long-pass filter (cut-off wavelength 900 nm) was used in our measurements to filter the pump as well as the silica Raman background. Other filters may be used which pass through longer wavelengths than the pump laser. These additional long pass filters may be needed to further reduce the scattered pump laser and silica Raman background.

The existence of the background may limit the sensitivity when measuring low-frequency vibrational modes (e.g., below 2000 cm$^{-1}$). In embodiments where the particle adhered to the microresonator is relatively large, forward scattered background generated inside the resonator is significantly stronger than that in the side scattering and reduces the sensitivity of the signal collection setup. Where forward scattering is strong, a sample for analysis may be placed on the outer edge of the resonator, and Raman signal may be collected in the upright direction (i.e., perpendicular to the plane) to suppress the scattered silica Raman background.

In a typical embodiment involving nanoparticles the Rayleigh scattering signal is proportional to $\propto d^6$ (where d is the diameter of the particle, $d \ll \lambda$) while the Raman signal is proportional to $\propto d^3$. Since spontaneous Raman scattering is an incoherent process, Raman signal intensity produced by different parts of the particle (e.g., different molecules) add up linearly. As a result, the Rayleigh-scattered silica background decreases much faster than the Raman signal as particle size reduces. The Rayleigh scattering also exhibits a more uniform angular pattern. For nanoparticles the limitation due to the silica Raman background can be significantly alleviated.

Since silica has low loss over the visible and ultraviolet regime, resonance Raman can be potentially applied to further improve the nanoparticle detection sensitivity.

The frequency of the laser can be tuned and its polarization can be optimized so that either TM or TE mode can be excited in the microtoroid. This enables embodiments of the invention to be used to perform a Raman polarization study, which contains information such as the orientation and chirality of molecules.

In addition, "double resonance" may be accomplished, in which both the laser and the Raman signal are resonant with the resonator. This could be accomplished by utilizing a tunable microresonator (e.g., thermal tuning by mounting the resonator chip on a small thermoelectric cooler) in addition to a tunable pump laser source. The double resonance could lead to further enhancement of the Raman signal.

B. Label-Free Particle Sensing by Fiber Taper Based Resonator Enhanced Raman Spectroscopy Embodiments also provide a fiber taper based method for label-free Raman sensing which exploits the interaction between adsorbed specimen and the exposed evanescence tail of guided pump light. To improve the sensitivity, resonator enhanced Raman spectroscopy may take advantage of the power build-up of a resonant mode in a cavity.

Optical fiber tapers provide a unique and versatile platform for sensing. Tapers can guide light while providing a relatively large evanescent field interaction length, which can be exploited for interrogating an adsorbed specimen or surrounding medium. In addition, their small size and strength, as well as their manufacturing ease and low cost, make tapers useful and practical for various sensing applications. In general, fiber taper based sensing is demonstrated using two types of configurations; either by direct evanescent field interaction with an analyte, by functionalizing the taper surface with molecular binding sites or field-enhancement nanomaterials. Non-functionalized fiber taper based sensing has been demonstrated in several detection modalities, for example, through surface absorption spectroscopy, fluorescent detection, transmission measurement, and intra-fiber modal interference spectroscopy. However, these methods usually cannot provide chemical selectivity.

Raman scattering spectroscopy is another commonly used sensing method, which can detect target molecules through their vibrational "fingerprint" spectra. Several fiber taper based sensing techniques have utilized Raman scattering for molecular detection. These methods primarily focus on the surface enhanced Raman scattering (SERS) approach, in which the taper surface is functionalized by adhering metallic particles. These techniques may demonstrate labelfree, highly sensitive chemically specific specimen detection. However, a major challenge lies in the control of the nanostructures on the functionalized taper surfaces across multiple sensors. The nanostructures, hence the relative enhancement, can vary between each sensor, which may require additional calibration and can impose added complexities in sensor production.

We provide fiber taper based Raman scattering spectroscopy as a label-free method for chemically selective sensing without the aid of functionalized fiber tapers. This includes Raman scattering signal from microspheres adhered to a fiber taper interacting with the evanescent pump laser field. While the detected Raman signal is relatively weak due to the typically small Raman scattering cross-section, this is enhanced by incorporating the fiber taper as part of a fiber ring-cavity. The Raman signal is enhanced by the cavity build-up of the resonant laser pump power, providing an alternative path towards sensitive chemical detection.

One embodiment is shown in FIG. 8, where a tapered optical fiber is positioned with the taper waist located at the focal plane of a micro-Raman imaging and signal collection system. Fiber tapers may be formed by heating single-mode optical fiber (Corning SM600) with a hydrogen torch and pulling the fiber through a pair of computer-controlled translational stages. A tunable diode laser may be coupled to the fiber taper and a photodiode used to monitor the transmission through the taper. The imaging and Raman signal collection system share a longworking-distance objective lens (for example, a Mitutoyo 50× Plan Apo, NA=0.55, W.D.=13 mm) to collect and image the scattered signal from a particle adhered to the fiber taper. A short pass filter with cutoff wavelength at 890 nm (Chroma 890SP) is used to reflect the Raman signal to a spectrometer (PI Acton SP-2500i) while passing wavelengths shorter than 890 nm for imaging on a charge coupled device (CCD) imager. Short pass filters of other wavelengths may also be used. A long pass filter is positioned in front of the entrance slit of the spectrometer to further filter residue pump laser light.

To first demonstrate the Raman sensing capability, a particle is delivered to the taper waist and the micro-Raman system is aligned and focused to the particle. The procedure for attaching a particle to the fiber taper is illustrated in FIG. 9, parts (a) through (d). In FIG. 9, part (a), for clarity in demonstration, a large 10-μm-diameter polystyrene (PS) microsphere is first attached by electrostatic force to the end of a fiber probe (which is separately fabricated by tapering a fiber using a fusion splicer and mounted on a three-dimensional translational stage), and positioned near a fiber taper with a diameter of approximately 1 μm. The fiber probe is then moved towards the taper to deposit the 10-μm PS microsphere onto the side of the taper (FIG. 9, part (b)). The microsphere is held in place by electrostatic force and remains quite stable on the taper. In FIG. 9, part (c), a 2-μm diameter microsphere is adhered to the fiber taper and in FIG. 9, part (d) adhesion of several 2-μm microspheres above and below the fiber taper is demonstrated. In each of the images, the object blur in the top left corner is the out of focus fiber probe used for microsphere delivery.

The evanescent field that "leaked" out from the fiber taper can interact with the adsorbed particles. In particular, the Raman scattering signal produced from the particles can provide molecule-specific "fingerprint" spectroscopic response to uniquely identify the chemical composition of the adhered particles for label-free sensing. In FIG. 10, Raman spectra obtained from collecting the scattered signal from a 2-μm PS microsphere attached to a fiber taper is shown. A characteristic Raman feature of interest for PS is located at approximately 3050 cm$^{-1}$. The wavenumber difference from previous reporting is due to a large spectrometer entrance slit (250 μm) which improves the throughput but also reduces the resolution of the observed spectra.

To demonstrate the collected signal is indeed Raman generated from the PS microsphere, plots are shown in FIG. 10(A) where the pump laser was tuned from 766.2 nm to 772.8 nm. The spectra were acquired on the spectrometer with integration times of 30 seconds. The coupled laser power to the fiber taper at each wavelength was 8.6 mW and 10 mW, respectively. The figure shows that while the wavelength of the pump laser is tuned, the PS peak moves with the pump maintaining a Raman shift of around 3050 $cm^{-1}$.

Additionally, the broad background observed at shorter wavelengths occurs from the presence of a strong silica Raman scattering background that is generated from within the fiber taper and scattered by the microsphere, which peaks at around 440 $cm^{-1}$ (i.e., 13.2 THz). The long-pass filter (cut-off wavelength 900 nm) is used to filter, in addition to the pump laser, most of the broad silica background. This filter was replaced with an 810 nm long pass filter to observe more clearly the broad silica Raman background as shown by the overlapping curves (black) for each spectra in FIG. 10(A). When the microsphere used is relatively large, forward scattering is strong (in this case, defined as the radial direction from the contact point of the microsphere on the taper through the center of the microsphere). For this reason, the microsphere when large may be placed on the side edge of the fiber taper and Raman signal was collected in the upright direction (cf., FIG. 8) to suppress the scattered silica Raman background. The existence of this background may limit the sensitivity especially when measuring low-frequency vibrational modes.

To further demonstrate chemical sensitivity, FIG. 10(B) shows the comparison of Raman spectra measured from a PS and a Poly-methyl methacrylate (PMMA) microsphere. During the experiment, the laser was tuned to 765 nm and coupled power was maintained at ~6.5 mW. First, a 1-µm PS sphere was adhered to the fiber and a 30 second integration spectra (bottom curve) was collected exhibiting similar features to the 2 µm PS microsphere results in FIG. 10(A). Next, the PS microsphere was removed and a 1-µm-diameter PMMA microsphere was attached to the taper with similar pump conditions to the PS sphere measurement, and again a 30 second integration spectral measurement was recorded (top curve). A distinctive PMMA Raman peak centered at 2912 $cm^{-1}$ was observed as shown in FIG. 10(B). These results clearly demonstrate the label-free particle sensing capability.

C. Fiber Ring Resonator Enhanced Raman Spectroscopy

Unlike in traditional Raman spectroscopy implemented by using a free-space excitation beam, the use of a fiber taper for guiding the pump laser field naturally creates a unique opportunity to "recycle" unused pump power by incorporating the taper into a fiber ring resonator. The power of a resonant mode circulating inside the ring cavity can be significantly enhanced, leading to enhanced Raman scattering from an adhered specimen. As FIG. 11 shows, we have developed a fiber ring resonator that consists of a 50/50 fiber coupler (Thorlabs FC-780-50B, measured 53/47 ratio at λ=761 nm) for coupling the tunable laser to the cavity, a fiber taper, and a fiber polarization controller used to compensate for fiber birefringence in order to maintain the polarization state after each round trip.

A photodiode is used to monitor the transmission and provides feedback signal to lock the laser to a resonant frequency of the fiber cavity. By modulating the laser frequency and simultaneously detecting the transmission signal with a lock-in amplifier, the slope of the transmission spectrum can be determined. A control signal is then applied to the tunable laser to lock its frequency to the minimum transmission position (i.e., zero slope), at which a resonator mode is excited. Demonstration of the frequency locking is shown in FIG. 12, where a 2-µm PS microsphere is adhered to the fiber taper similarly to that prepared in the Raman sensing experiments previously described. Due to the bulkiness of the cavity, the system is sensitive to the environment perturbations, resulting in significant noise in the collected signal.

In FIG. 12 the transmission signal is plotted as the laser frequency is scanned by a piezo actuator before the locking mechanism is activated. The figure shows several resonant modes that span multiple free spectral ranges of the fiber cavity. One may then activate frequency locking using the configuration described in FIG. 11. The transmission signal is locked near its minimum value as is shown in the bottom curve of FIG. 12, indicating the excitation of a resonant mode.

After locking the laser to the resonance of the ring-cavity, one may perform fiber ring resonator enhanced Raman spectroscopy. The results are presented in FIG. 13. During our experiment, a 2-µm PS sphere was adhered to the fiber taper. Coupled pump power in the fiber was maintained at 2.75 mW and the micro-Raman collection setup remained the same for each of the measurements. The Raman spectrum obtained without the fiber ring resonator (i.e., directly from the taper, cf. FIG. 8) is given by the bottom curve. The bottom curve shows the Raman spectrum measured with the fiber ring resonator, but in this case the frequency of the laser was constantly scanned rather than locked to demonstrate the difference between scanning and cavity locking. Finally, the laser frequency was locked to match a resonant frequency and the measured Raman spectrum of the adhered PS microsphere is plotted by the black curve.

The comparison shows that approximately a 1.4 to 1 enhancement ratio is achieved in signal over the background for the PS 3050 $cm^{-1}$ Raman peak (located at approx. k=987 nm) and the collected scattered intensity of the laser (tuned to 761 nm) indicates a similar enhancement ratio. Also, the figure shows an enhanced signal when comparing the taper design (red curve) to the resonator design when wavelength is scanned (blue curve), however this is due to the difference in input power (the 50/50 coupler effectively reduces the coupled power to the cavity). While these results indicate albeit a modest enhancement factor in our proof-of-concept study, significant room exists for improving the enhancement factor.

To gain additional insight into the enhanced Raman scattering by a ring resonator, one may analyze the resonance enhancement of the ring cavity. The power transmittance (T) and the power build up factor (B) of the resonator are given by, $$T = \left| \tau - \frac{\kappa^2 \delta e^{i\phi}}{1 - \delta \tau e^{i\phi}} \right|^2 \quad (1)$$

$$B = \left| \frac{i\kappa}{1 - \delta \tau e^{i\phi}} \right|^2 \quad (2)$$

where τ and κ are respectively the transmission coefficient and the coupling coefficient of the fiber coupler, δ is the field amplitude transmittance per round trip, and Ø is the round-trip phase delay. To model the fiber ring resonator configured for the experiment, κ~0.64, and τ~0.7 corresponding to a fiber coupler insertion loss of 10% (κ²+τ²=0.9,) as well as estimated losses within the cavity (taper, scattering from adhered particle, in-line fiber polarizer, fiber splices) of 55% (δ~0.67) were used. Using these conditional parameters, the simulation for the ring resonator is shown in FIG. 14 where the transmission coefficient T and the cavity build up factor B are plotted. Given the conditions associated with the experiment, the maximum attainable gain in cavity circulating power shown in the simulation is approximately 1.78 at cavity resonance, which is comparable to our experimental observation. In typical embodiments the cavity circulating power at cavity resonance is between 1.70 and 1.90.

The work demonstrates a method for Raman spectroscopic sensing using tapered optical fibers. Chemical selectivity is demonstrated by detecting the Raman spectra of two different polymer microspheres adhered to a fiber taper with particle diameters down to µm. Resonator enhanced Raman scattering spectroscopy was also explored using a fiber taper as part of a fiber ring-cavity. A signal enhancement factor of approximately 1.4 was observed to demonstrate the proof of principle. Although significant cavity losses in our ring cavity study limited the attainable cavity enhancement, much greater enhancement could be potentially achieved using high-Q microresonators (e.g., microsphere or microtoroid whispering gallery mode resonators).

Note that the cavity power build-up factor of a high-Q whispering gallery mode microresonator is given by:

$$B = \frac{4Q_{ex}}{\left(\frac{Q_{ex}}{Q_0} + 1\right)^2} \frac{\Delta v}{\omega_0}$$

where $\Delta v$ is the cavity free spectral range, $Q_0$ and $Q_{ex}$ are the Q's accounting for the intrinsic loss and the external coupling respectively, and $\omega_0$ is the resonant angular frequency. For example, utilizing microresonators with a diameter of ~40 µm and $Q \sim 10^8$, Raman scattering potentially can be enhanced by up to five orders of magnitude. This integration of enhanced Raman sensing with microresonators and other resonator sensing methods (e.g., quantitative detection through absorption, mode-splitting) allows for comprehensive assay of adhered particles, opening a new paradigm for label-free, ultrasensitive biochemical sensing.

III. Microresonator Enhanced Optical Active Raman Spectroscopy

A further embodiment uses microresonators to enhance optical active Raman spectroscopy. Many bio-molecules (e.g., proteins, sugars) and bio-nanoparticles (e.g., viruses) are chiral. Probing their stereochemical information and identifying their chirality (i.e., differentiating one enantiomer from the other) are critical for many applications. Amongst several commonly used methods (e.g., circular dichroism, optical rotatory dispersion), Raman optical activity (ROA) has proven to be a powerful technique in that it can probe the stereochemical information of a whole molecule rather than just the chromophores.

ROA measures the small difference between the Raman spectra produced by right and left circularly polarized pump beams, or the small difference between the right and left circularly polarized components of the Raman signal produced by a linearly polarized pump beam. One challenge of the ROA measurement is that the signal is very weak, e.g., about three orders of magnitude less than a conventional Raman signal. As an example, a typical measurement by a commercial instrument can require up to 80 minutes of exposure time. Sensitivity of ROA in a microtoroid microresonator should improve by several orders of magnitude.

Either TE or TM mode can be excited in a microtoroid or other resonator by tuning the laser frequency and optimizing the polarization state (as these two types of modes have different resonant frequencies). After being collected by the objective, the polarization state of the Raman signal from a chiral nanoparticle can be analyzed. In particular, one may measure the spectral intensity difference between the right and left circularly polarized components, i.e., the spectrum of the fourth Stokes parameter $S_3$.

It can be shown that the ratio of $S_3/S_0$ ($S_0$: the first Stokes parameter) is equivalent to the circular intensity differential (i.e., $(I^R-I^L)/(I^R+I^L)$, where $I^R$ and $I^L$ are intensities of the scattered light produced by using right or left circularly polarized pump beam respectively), which is often used in Raman optical activity measurements. The ROA spectra ($S_3/S_0$) are different for the two enantiomers. Therefore, this can be used to identify the chirality of the nanoparticle. Due to the enhanced Raman scattering by the resonators, the signal to noise ratio of the ROA spectra can be better than that obtained using standard ROA spectroscopy.

Figure 3:
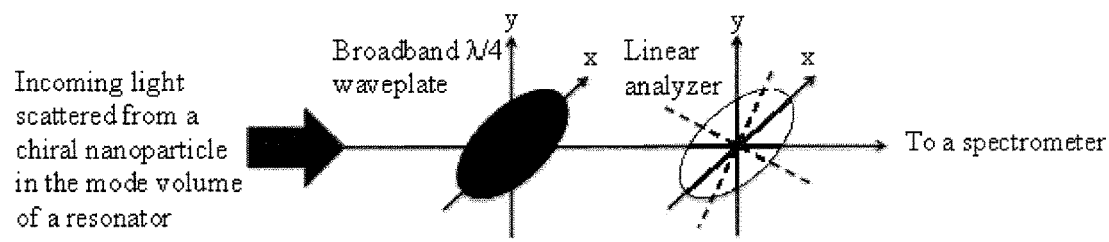
FIG. 3 is a schematic diagram showing the measurement of Stokes parameters for resonator enhanced optical active Raman spectroscopy.

FIG. 3 shows a method used to measure the Stokes parameter. Incoming light scattered from a chiral nanoparticle in the mode volume of a resonator first passes through a broadband $\lambda/4$ waveplate (e.g., Fresnel Rhomb or other birefringence based broadband waveplate), whose fast axis is along the x axis. A linear polarizer is placed behind the waveplate. The ratio of $S_3/S_0$ can then be measured by performing two subsequent measurements with the transmission axis of the polarizer aligned along the 45° or 135° (with respect to the x axis) directions respectively, as indicated by the dashed lines in the figure. It can be shown that the ROA spectrum $S_3/S_0$ is given by the following equation:

$$\begin{cases} I(45°) = \frac{1}{2}(S_0 + S_3) \\ I(135°) = \frac{1}{2}(S_0 - S_3) \end{cases} \Rightarrow \frac{S_3}{S_0} = \frac{I(45°) - I(135°)}{I(45°) + I(135°)} \quad (2)$$

where $I(45°)$ and $I(135°)$ refer to the measured spectral intensity with the linear polarizer aligned at 45° and 135° directions respectively.

IV. Microtoroid Resonator Enhanced Hyper Raman Spectroscopy

Figure 4A:
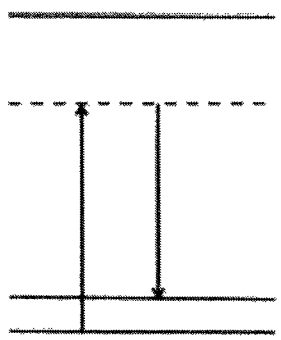
FIG. 4 shows energy level diagrams illustrating the difference between conventional and hyper Raman processes.
Figure 4B:
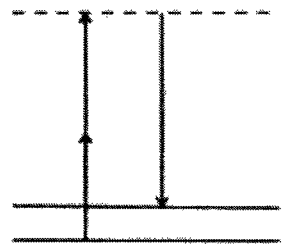

Embodiments may incorporate an ultrahigh-Q microtoroid microresonator in conjunction with hyper Raman spectroscopy. FIG. 4 shows the energy diagrams involved in conventional and hyper Raman processes. In a hyper Raman process, two pump photons rather than one are annihilated to generate a Raman photon. The main merit of hyper Raman is that it can probe vibrational modes which are both infrared and Raman inactive.

An example showing utility of hyper Raman is the twisting frequency in ethylene, which can only be probed by using hyper Raman. A major limitation of hyper Raman is its sensitivity. The signal strength is much weaker than that of conventional Raman. Since the signal power depends on the pump power quadratically, an enhancement factor of $G^2$ is expected. In some embodiments up to ten orders of magnitude enhancement can be achieved.

A sample experimental system that may be used in this embodiment is similar to the one shown in FIG. 1 except that the signal at near the second harmonic frequency of the pump will be monitored. Two-photon resonance (i.e., the virtual level shown in FIG. 4(B) becomes a real level) can be used to further enhance the hyper Raman signal.

V. Microtoroid Resonator Enhanced Coherent Raman Spectroscopy

A further embodiment provides microresonator enhanced coherent Raman techniques, specifically, coherent anti-Stokes Raman scattering (CARS) and stimulated Raman scattering (SRS). CARS and SRS can have significantly improved sensitivity compared with spontaneous Raman scattering. In addition, the CARS signal lies on the shorter wavelength side of the pump and is therefore immune to the scattered silica Raman background or possible one-photon excited fluorescence background.

CARS is a four wave mixing process resonantly enhanced by molecular vibrational response. In a CARS process, a pump beam at angular frequency $\omega_p$ and a Stokes beam at $\omega_s$ can coherently excite molecular vibration if the frequency difference between the pump and the Stokes matches the molecular resonance frequency (i.e. $\Omega=\omega_p-\omega_s$). A probe beam (usually also at $\omega_p$, e.g., same as the pump) then interacts with the vibrating molecules and produces an anti-Stokes beam at $\omega_{as}=\omega_p+\Omega=2\omega_p-\omega_s$. It has been reported that more than five orders of magnitude improvement in conversion efficiency (compared with spontaneous Raman) can be achieved. More specifically, the anti-Stokes field is given by $$E_{as} \propto \chi^{(3)} E_p(\omega_p) E^*_s(\omega_s) E_{pr}(\omega_p) \quad (3)$$

where $\chi^{(3)}=\chi_{NR}^{(3)}+A/(\omega_p-\omega_s-\Omega+i\Gamma)$ is the third order nonlinear susceptibility and contains a nonresonant background term $\chi_{NR}^{(3)}$ and a molecular vibrational resonance term, $E_{as}$, $E_p$, $E_s$, and $E_{pr}$ are the fields of the anti-Stokes, pump, Stokes, and probe, respectively.

Figure 5:
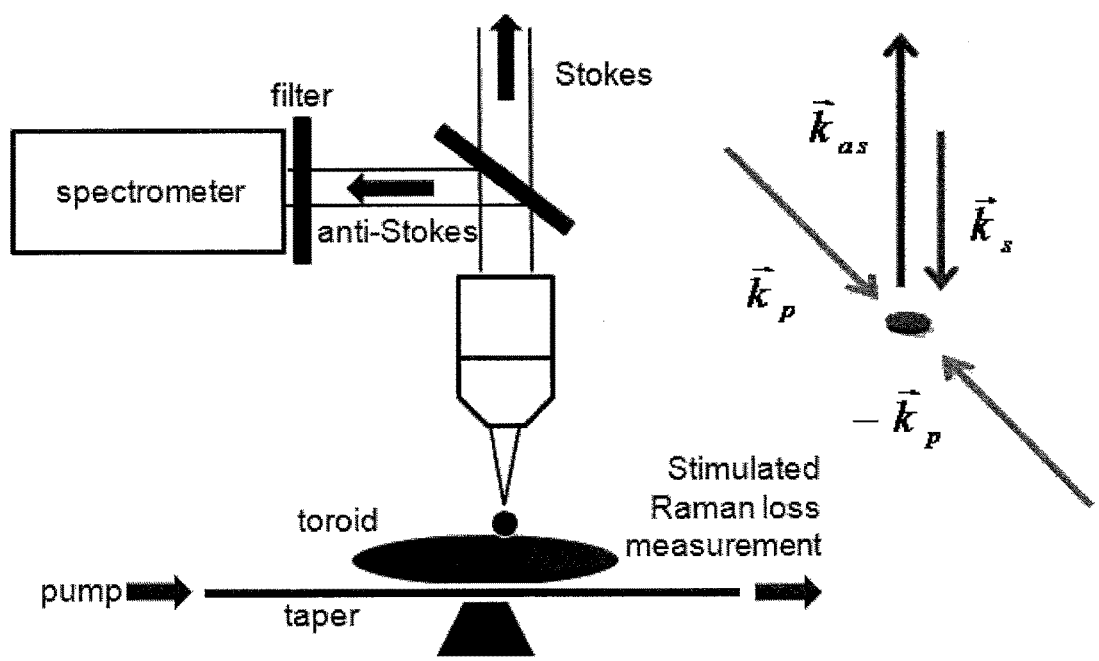
FIG. 5 illustrates an embodiment of microresonator enhanced coherent Raman spectroscopy.

FIG. 5 (left) shows a schematic diagram of the proposed microresonantor enhanced CARS experimental system. Considering that the photon lifetime in a microresonator is in nanosecond scale, nanosecond laser systems may be utilized. As shown in FIG. 5 a nanosecond pump beam is coupled into a microtoroid. Since the pump (also used as probe) power is enhanced inside the microresonator, the CARS signal strength is enhanced by $G^2$. The tunable (e.g., an optical parametric oscillator) or broadband (e.g., supercontinuum) Stokes beam is introduced through free space and focused by using an objective.

The advantages to this are twofold: first the Stokes can be a broadband beam (i.e., supercontinuum) or continuously tunable to obtain a broad-band CARS spectrum; and second the nonresonant four wave mixing background that would be generated in the microtoroid by copropagating the pump and Stokes can be avoided. If the pump is a standing wave (e.g., due to Rayleigh scattering induced mode-splitting) and comprises opposing wave vectors, the anti-Stokes signal can be epi-detected, minimizing the phase mismatch as shown in FIG. 5 (right). For nanoparticles small phase mismatch is also allowed due to a relaxed phase matching condition.

Unlike CARS, SRS does not have nonresonant background. High-sensitivity SRS microscopy has recently been demonstrated. Here we propose to explore micro-resonator enhanced SRS spectroscopy. The stimulated Raman gain of the Stokes and the stimulated Raman loss of the pump are given by:

$$\Delta I_s \propto N\sigma I_p I_s$$

$$\Delta I_p \propto -N\sigma I_p I_s \quad (4)$$

where N is the molecular number, $\sigma$ is the Raman scattering cross section, $I_p$ and $I_s$ are the intensities of the pump and the Stokes respectively. Since the pump power is enhanced by a factor of G, the SRS signal, which depends on the pump linearly, is also enhanced by G. To detect $\Delta I_p$, the intensity of the Stokes can be modulated. The stimulated Raman loss manifests the same modulation and can therefore be detected by lock-in amplification. Similar method can be used to measure $\Delta I_s$. The SRS spectrum can then be obtained by scanning the frequency of the Stokes.

VI. Fiber Ring Resonator Enhanced Raman Spectroscopy

Embodiments of the invention may be provided with tapered optical fibers, or tapered optical fibers may be used with conventional sensing methods and devices. Optical fiber tapers provide a unique and versatile platform for sensing. Tapers can guide light while providing a relatively large evanescent field interaction length, which can be exploited for interrogating an adsorbed specimen or surrounding medium. In addition, their small size and strength, as well as their manufacturing ease and low cost, make tapers useful and practical for various sensing applications. In general, fiber taper based sensing is demonstrated using two types of configurations: either by direct evanescent field interaction with an analyte, or by functionalizing the taper surface with molecular binding sites or field-enhancement nanomaterials. Nonfunctionalized fiber taper based sensing has been demonstrated in several detection modalities, for example, through surface absorption spectroscopy, fluorescent detection, transmission measurement, and intra-fiber modal interference spectroscopy. However, these methods usually cannot provide chemical selectivity.

Here we propose fiber taper based Raman scattering spectroscopy as a label-free method for chemically selective sensing without the aid of functionalized fiber tapers. Raman scattering from microspheres adhered to a fiber taper interacting with the evanescent pump laser field is demonstrated. Further, we propose a method for enhancement of the Raman signal by incorporating the fiber taper as part of a fiber ring-cavity. The Raman signal can be enhanced by the cavity build-up of the resonant laser pump power, providing an alternative path towards sensitive particle detection.

One experimental setup is shown in FIG. 6(A), where a particle is deposited on the waist of a fiber taper. A Raman signal collection system is positioned to collect scattered light. FIG. 6(B) shows an image of a typical experimental configuration, where a 2 μm diameter polymer microsphere is adhered to a fiber taper.

The taper was drawn by heating with a hydrogen torch and pulling it by two computer controlled stages, and the particle was delivered to the taper by another fiber probe mounted to a three-dimensional stage and is held place by electrostatic forces. FIG. 6(c) shows Raman spectra obtained from collecting scattered light from a 1 μm polystyrene sphere (PS) adhered to a taper (pump laser ~4-6 mW, 30 sec. integration times). The characteristic Raman feature of interest for PS is explored in this figure (at 3060 cm$^{-1}$) and tuning of the pump laser across several wavelengths from 753 to 777 nm demonstrates the captured signals are indeed Raman. Additionally, the broad background observed from 900-950 nm occurs from the presence of a strong silica Raman scattering background that is generated from within the fiber taper, which peaks at around 440 cm$^{-1}$ (i.e., 13.2 THz).

A long-pass filter (cutoff at wavelength 900 nm) blocks most of the silica Raman scattering background and pump laser (small breakthrough). The existence of this background may limit the sensitivity especially when measuring low-frequency vibrational modes. Also, since the microsphere used in our preliminary study is relatively large, forward scattering is strong. For this reason, the microsphere was placed on the side edge of the fiber taper and Raman signal was collected in the upright direction to suppress the scattered silica Raman background. FIG. 6(d) shows the comparison of Raman spectra measured from a 1 μm PS and a 1 μm Poly-methyl methacrylate (PMMA) microsphere individually adhered to the fiber taper. Once again, the PS microsphere produced Raman signal at 3060 cm$^{-1}$ while the PMMA microsphere Raman signal was detected at 2959 cm$^{-1}$.

The sensitivity of the fiber taper based Raman spectroscopy can be further enhanced by incorporating the fiber taper in a fiber ring resonator as shown in FIG. 7. The resonator includes a fiber coupler for coupling a tunable laser to the cavity, a fiber taper, and a fiber polarization controller used to compensate for fiber birefringence to maintain the polarization state after each round trip. A photodiode is used to monitor the transmission and provides feedback signal to lock the laser to a resonant frequency. Specifically, by modulating the laser frequency and simultaneously detecting the transmission signal with a lock-in amplifier, the slope of the transmission spectrum can be determined. A control signal is then applied to the tunable laser to lock its frequency to the minimum transmission position (i.e., zero slope), at which a resonator mode is excited. Similarly, the power of the resonant mode circulating inside the fiber ring resonator can be enhanced, leading to enhanced Raman scattering from a specimen adhered to the fiber taper.

Any documents referenced above are incorporated by reference herein. Their inclusion is not an admission that they are material or that they are otherwise prior art for any purpose. If any of those documents is contradicted by this specification, this specification controls.

We claim:

1. A resonator-enhanced Raman spectrometer, comprising:
    at least one laser light source, wherein said at least one laser light source is a tunable pump laser source and configured to generate a light with a frequency and a polarization state;
    a polarization controller in series with each of said at least one laser light source;
    at least one of an optical waveguide and free-space optics in series with each of said polarization controller for delivery of optical excitation sources;
    at least one resonator coupled to said optical excitation sources, wherein said at least one resonator has a resonant mode;
    a photodetector operably connected to said at least one resonator;
    a spectragraph for analysis of information from said at least one resonator; and
    an imaging device in cooperation with said spectragraph, wherein the tunable pump laser source and the polarization controller are configured to selectively excite a resonant transverse magnetic mode or a resonant transverse electric mode of said at least one resonator.

2. The spectrometer of claim 1, wherein said at least one resonator is selected from at least one member of the group consisting of a microtoroid, a microsphere, micro-bubble, a micropost, a microdisk, a Fabry Perot cavity, a ring resonator, a metamaterials and photonic crystal cavity.

3. The spectrometer of claim 1, wherein said frequency of said at least one laser light source is locked to said resonant mode of said at least one resonator.

4. The spectrometer of claim 1, wherein said at least one resonator is a tunable microresonator, wherein said at least one resonator and said at least one laser source are tunable to be doubly resonant with a Raman signal.

5. The spectrometer of claim 1, wherein the at least one resonator further comprises a plurality of microresonators, wherein said plurality of microresonators are fabricated on a single chip.

6. The spectrometer of claim 1, further comprising a tapered optical waveguide coupled to said at least one resonator and configured to guide said optical excitation sources into said at least one resonator.

7. A method for resonator-enhanced Raman spectrometry, comprising:
    determining resonant frequencies of one or more resonator in a Raman spectrometer;
    selectively exciting a resonant transverse magnetic mode or a resonant transverse electric mode of light from the one or more resonator;
    determining quality factors of said one or more resonator; and
    obtaining a Raman spectrum of a specimen.

8. The method of claim 7, wherein said one or more resonator is selected from at least one member of the group consisting of a microtoroid, a microsphere, micro-bubble, a micropost, a microdisk, a Fabry Perot cavity, a ring resonator, a metamaterials and photonic crystal cavity.

9. The method of claim 7, wherein said Raman spectrometer is selected from the group consisting of a spontaneous Raman spectrometer, an optical active Raman spectrometer, a hyper Raman spectrometer, and a coherent Raman including a coherent anti-Stokes, Raman scattering spectrometer and a stimulated Raman scattering spectrometer.

10. The method of claim 7, further comprising monitoring a signal from a fiber taper; determining a resonant frequency of said one or more resonator from said signal from said fiber taper, and locking a frequency of a spectrographic laser to said resonant frequency of said one or more resonator.

11. A resonator-enhanced optical active Raman spectrometer, comprising:
    at least one tunable polarized pump source configured to generate a light with a frequency and a polarization state;
    a polarization controller in connection with said at least one tunable polarized pump source;
    at least one resonator coupled to said at least one polarized pump source, wherein said at least one resonator has a resonant mode;
    a photodetector operably connected to said at least one resonator; and
    a spectragraph for analysis of information and measurement of a Stokes parameter from said at least one resonator,
    wherein the tunable polarized pump source and the polarization controller are configured to selectively excite a resonant transverse magnetic mode or a resonant transverse electric mode of said at least one resonator.

12. The resonator-enhanced optical active Raman spectrometer of claim 11, wherein said frequency of said at least one polarized pump source is locked to said resonant mode of said at least one resonator.

13. The resonator-enhanced optical active Raman spectrometer of claim 11, wherein said at least one resonator is a tunable microresonator, wherein said at least one resonator and said at least one polarized pump source are tunable to be doubly resonant with a Raman signal.

14. A resonator-enhanced hyper Raman spectrometer, comprising:

a laser light source, wherein said laser light source is a tunable pump laser source and configured to generate a light with a frequency and a polarization state;

a polarization controller in series with the laser light source;

a tapered optical waveguide in series with the polarization controller;

a photodetector in series with the tapered optical waveguide;

a microresonator in communication with the tapered optical waveguide, wherein said microresonator has a resonant mode; and a spectrometer collecting data from the signal, wherein the tunable pump source and the polarization controller are configured to selectively excite a resonant transverse magnetic mode or a resonant transverse electric mode of said microresonator.

15. The resonator-enhanced hyper Raman spectrometer of claim 14, wherein the frequency of the laser light source is locked to the resonant mode of the microresonator.

16. The resonator-enhanced hyper Raman spectrometer of claim 14, wherein the microresonator is a tunable microresonator, wherein the microresonator and the laser light source are tunable to be doubly resonant with a hyper Raman signal.

17. A nanoparticle sensor, comprising: a) a Raman spectrometer, said Raman spectrometer providing identification of at least one of molecules and particles through molecular vibrational spectroscopy; and b) in communication with the Raman spectrometer, an ultra-high-Q Whispering Gallery mode microresonator providing Rayleigh scattering based detection and measurement of the at least one of molecules and particles using interactions of said molecules and particles with said Whispering Gallery mode; and a polarization controller in connection with a tunable laser light source of the Raman spectrometer, the tunable laser light source configured to generate a light with a frequency and a polarization state;

wherein the microresonator has a resonant mode, and wherein the tunable laser source and the polarization controller are configured to selectively excite a resonant transverse magnetic mode or a resonant transverse electric mode of the microresonator.

18. The nanoparticle sensor of claim 17, wherein the at least one of molecules and particles are label-free.

19. The nanoparticle sensor of claim 17, wherein the Raman spectrometer is selected from the group consisting of a spontaneous Raman spectrometer, an optical active Raman spectrometer, a hyper Raman spectrometer, and a coherent Raman including a coherent anti-Stokes Raman scattering spectrometer and a stimulated Raman scattering spectrometer.

20. The nanoparticle sensor of claim 17, wherein the microresonator is in an environment selected from the group consisting of a liquid environment and a gaseous environment.

21. The spectrometer of claim 17, wherein the frequency of the laser light source is locked to the resonant mode of the microresonator.

* * * * *